United States Patent [19]

Bauer

[11] 4,193,198
[45] Mar. 18, 1980

[54] ORGANIZER FOR DENTAL CLAMPS

[76] Inventor: Philip J. Bauer, 214 Slice Dr., Stamford, Conn. 06907

[21] Appl. No.: 963,773

[22] Filed: Nov. 27, 1978

[51] Int. Cl.² .............................................. A61C 3/00
[52] U.S. Cl. .............................. 433/77; 211/DIG. 1; 211/13
[58] Field of Search ............ 248/206 A; 211/DIG. 1, 211/13; 32/40 R

[56] References Cited

U.S. PATENT DOCUMENTS 3,153,177 10/1964 McFadyew .................. 211/DIG. 1
4,150,752 4/1979 Breining ................................. 211/13

Primary Examiner—Robert Peshock
Attorney, Agent, or Firm—Spencer E. Olson

[57] ABSTRACT

A rack for supporting and systematically organizing dental clamps according to shape and size includes a support and a plurality of posts extending generally upwardly therefrom, the posts each having at least one partially circumferential slit disposed essentially perpendicular to the axis of the post, and containing a permanent magnet exposed at the inner end of the slit. In use, the bow portion of a clamp is placed in a slit, the slit serving to mechanically support the clamp on the post and the magnet serving to retain the clamp in the slit, even though the rack be jostled while being moved from one place to another, or tipped, or subjected to any other action that would tend to dislodge the clamp from the slit if not otherwise held.

8 Claims, 6 Drawing Figures

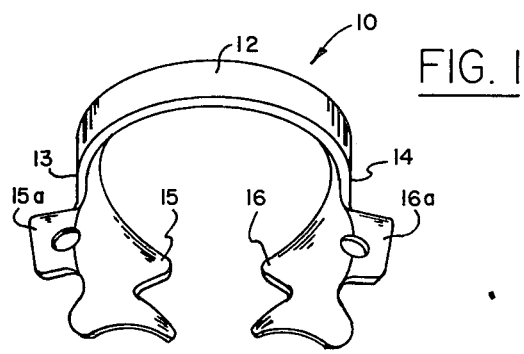
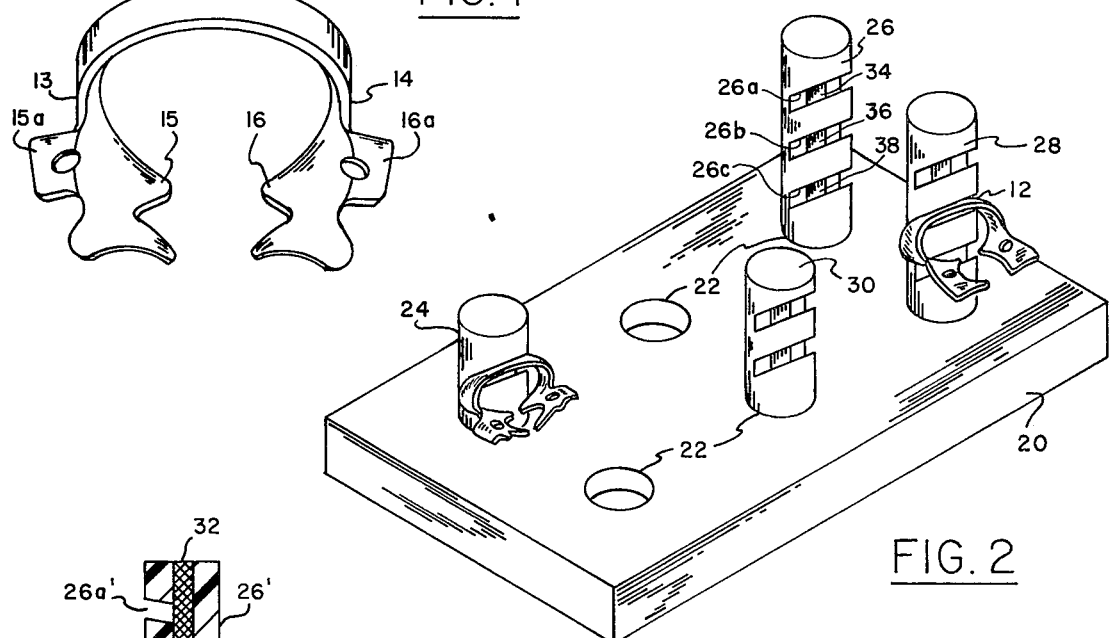
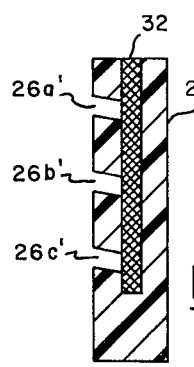
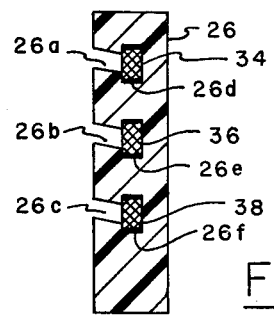
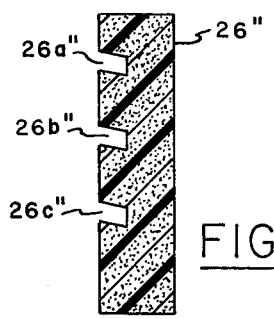
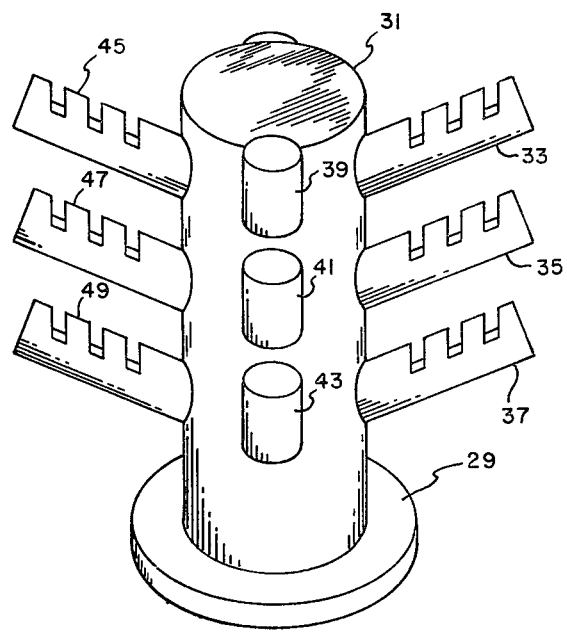

ORGANIZER FOR DENTAL CLAMPS

BACKGROUND OF THE INVENTION

This invention relates to an accessory useful in dental practice for organizing dental clamps of various shapes and sizes in such a way that the dentist can select the type of clamp that he knows from experience is needed for the particular procedure at hand.

In certain operations, for example in root canal work, dentists find it necessary to isolate the tooth being worked on from mouth saliva and moisture. Usually this is accomplished by means of a dam in the form of a thin sheet of rubber having a small hole punched therein to accommodate the tooth being worked on. The dam is held by a clamp in a depressed position over the gum to expose the tooth at the work area. With the dam applied and held in position by the clamp, the dentist is then free to work on the tooth without fear of moisture or foreign matter interfering with or contaminating the operation. Typical rubber dam clamps in present use are constituted by a bow spring whose legs are joined to a pair of jaws or "beaks" shaped to engage a tooth, the bow spring being inwardly biased, whereby the jaws are normally closed. Such clamps are commercially available in a variety of shapes and sizes so as to fit teeth of different shapes and sizes and are formed of magnetic metal of a thickness so as to be relatively rigid.

In the interest of efficiency in selecting the desired clamp from a collection of closely similar clamps, it is desirable to organize a group of clamps according to size and shape in such a way that the dentist can select the type of clamp (usually identified by a characterizing number) that he knows from experience is needed for the procedure at hand. Among known techniques for organizing or segregating clamps is the use of a compartmented tray, not unlike a fishing tackle box, and placing clamps of different shapes and sizes in respective compartments. The compartments not usually being numbered or identified in any way, the dentist often has to pick up several clamps before he finds the one he is looking for, and in the process some clamps wind up in compartments other than the one to which they should have been returned. This obviously complicates the selection process the next time a clamp is needed. Moreover, if a tray is bumped or upset, the clamps wind up on the floor and again have to be sorted and returned to their appropriate compartments. This technique also has the disadvantage that one cannot tell at a glance the current inventory of this or that size or type of clamp.

Another known type of clamp organizer consists of a flat molded plastic slab having formed on the upper surface thereof a plurality of short upstanding posts of equal length, arranged in rows and columns and having graduated diameters on which the clamps are secured by springing the clamp slightly to spread apart its jaws so that it firmly engages a post of a diameter appropriate to that particular clamp. In commercially available organizers of this type the posts are very close to each other and when filled with clamps has an appearance not unlike that of a tray of finger rings in a jewelry store, except, of course, that the clamp stands up above the upper surface of the slab. This type of organizer has the disadvantage that it stresses the clamp while in storage, and does not afford easy selection of a particular type of clamp from the collection of closely spaced similarly shaped clamps.

The primary object of the present invention is to provide an organizer for dental clamps that overcomes the above-outlined shortcomings of available organizers and has the advantage of permitting visualization of the jaws of the clamps to facilitate selection and avoiding continued flexing of the box.

SUMMARY OF THE INVENTION

Briefly stated, this object is attained in a clamp organizer constituted by a support member and a plurality of posts extending generally upwardly therefrom. The posts are formed of a suitable rigid material, such as plastic, and each has at least one slit formed therein disposed in a plane essentially perpendicular to the axis of the post and extending at least partially about its circumference. Each post is either formed of magnetic material or contains one or more permanent magnets arranged to be exposed at least at the bottom of each slit.

In use, the bow portion of a clamp is placed in a slit, the slit serving to mechanically support the clamp on the post, and the magnet serving to retain the clamp in the slit, even though the organizer be jostled while being moved, or tipped, or subjected to any other action that would tend to dislodge the clamp from the slit. With the bow portion of the clamp thus supported in the slit, the jaws thereof project outwardly from the post to be readily visible, thereby to simplify the selection of a clamp having the correct jaw separation for the procedure at hand. The posts are preferably of different lengths, with each post having a number of spaced-apart slits appropriate to its length. The longer posts, having more slits than the shorter ones, may be used to store most frequently used types of clamps, and shorter posts may be used for less frequently used clamps. An important advantage of the organizer is that once the clamps are organized they stay organized, and the user can see at a glance the inventory of each of several types of clamp.

BRIEF DESCRIPTION OF THE DRAWINGS

Other objects, features and advantages of the invention will become evident, and its construction and operation better understood, from the following detailed description, to be read in conjunction with the accompanying drawings, in which:

FIG. 1 is a perspective view, greatly enlarged, of a typical dental clamp of the kind intended to be supported and organized by the clamp organizer of the invention;

FIG. 2 is a perspective view of a preferred embodiment of a clamp organizer in accordance with the invention;

FIG. 3 is an elevation cross-section view of one of the posts of the clamp organizer shown in FIG. 2;

FIG. 4 is an elevation cross-section view of a first alternative construction of the post;

FIG. 5 is an elevation cross-section view of a second alternative construction of the post; and FIG. 6 is a perspective view of an alternative form of a clamp organizer in accordance with the invention.

DESCRIPTION OF THE INVENTION

Referring now to FIG. 1, there is illustrated a dental clamp, generally designated by reference numeral 10, typical of the type intended to be supported by the accessory according to the invention. The clamp 10 is fabricated of a suitable magnetic spring metal and includes a bow spring constituted by an arched shaped yoke 12 having a pair of legs 13 and 14 depending therefrom. Legs 13 and 14 are joined to forwardly projecting jaws 15 and 16 whose confronting edges are profiled to form "beaks" that conform generally to the contours of a tooth. The outer edges of jaws 15 and 16 of this particular type of clamp have flanges 15a and 16a extending laterally therefrom, the flanges being concave to conform to the gum line; other types do not have such flanges. In the passive state of the clamp, the jaws have a predetermined spacing, and in applying it the jaws are spread apart and positioned over the tooth; when released, the jaws grip the body of the tooth. Clamps of this type are commercially available in a variety of sizes and with different profiles on the jaws 15 and 16, and a dentist usually has a collection of several of each type and size to accommodate to a variety of tooth sizes and contours. The various sized and shaped clamps are usually identified by a characterizing number, and through experience the dentist learns that a clamp of a certain number is best suited to a given procedure. Thus, for efficiency it is desirable that the dentist be able to readily visibly select a clamp of the correct number for the procedure at hand.

Referring now to FIG. 2, one embodiment of the clamp organizer according to the present invention includes a flat base member 20, preferably rectangular in shape as shown and formed, for example, of plastic material, and has a plurality of holes 22 formed therein which extend only part way through the base member. The holes 22 are arranged in rows and columns and are of a diameter to receive with a press fit an upstanding cylindrical post, four of which are shown at 24, 26, 28 and 30. As illustrated, the posts may be of different lengths, with the longer posts toward the "back" of the base member, short ones in the front, and posts of intermediate length in between. Typically, the base member may be three inches by five inches, and the posts one-half inch in diameter and varying in length from about one inch to about three inches.

The posts, which are all of the same general construction, may take a variety of forms, three alternative forms of one of the longest posts, post 26 in FIG. 1, being illustrated in FIGS. 3, 4 and 5. The post shown in FIG. 3 is cylindrical in shape and is preferably molded, as by injection molding, from a slightly deformable plastic material, and is formed with three slits 26a, 26b and 26c which extend radially inwardly and downwardly at a slight angle to the horizontal and communicate with respective magnet-receiving cavities 26d, 26e and 26f of generally cubical shape disposed approximately along the longitudinal axis of the post. The slits are of a width to allow the insertion therethrough of a small permanent magnet of generally cubical shape, shown at 34, 36 and 38, into its respective magnet-receiving cavity. While the outer opening of the slit extends approximately half way around the post, the objectives of the invention are achieved by exposure of the magnets to a relatively small portion of the inner end of the slit. To facilitate insertion, the magnets are preferably inserted shortly following removal of the post from the mold while it is still relatively warm and more pliable than when fully cooled. The slight inclination of the slits provides a somewhat better mechanical support for the bow portion of a clamp inserted therein than if the slits were horizontally oriented and is therefore preferred, but because of the additional holding action of the magnet, horizontally disposed slits are also quite satisfactory.

In use, as illustrated in FIG. 2, the bow portion 12 of the clamp is placed in a slit, the slit being sufficiently deep that when the clamp is in engagement with the magnet the slit mechanically supports the bow over a substantial portion of its width, and the magnet by magnetic attraction serves to retain the clamp in the slit, even though the organizer be jostled while being moved from one place to another, or subjected to other action that would tend to dislodge the clamp from the slit if not otherwise held. With the bow portion of the clamp supported in the slit, the jaws of the clamp project outwardly from the post to be readily visible, thereby to simplify the selection of a clamp having the correct jaw separation (a criteria usually used) for the procedure at hand. Although the posts are shown in FIG. 2 with the open ends of the slits facing toward the right (primarily for clarity of illustration of the features of the posts), the posts may have other rotational orientations to maximize the visibility of the jaw portions of the clamps supported thereon. The number of slits per post may vary from one to say four, typically separated by about one-half inch, with the lowermost slit at least one-half inch above the base. The longer posts (with more slits) may be used to organize and "store" a clamp of the type most frequently used, and shorter ones may be used for only occasionally used types. An important advantage of this construction is that once the clamps are organized, they stay organized, and the dentist can see at a glance his inventory of each of several types of clamp.

FIG. 4 illustrates a first alternative construction of the post which is functionally equivalent to the construction shown in FIG. 3. The cylindrical post is preferably molded, as by injection molding, from a suitable plastic material to have three slits 26a', 26b' and 26c' extending radially inwardly and slightly downwardly to approximately the central axis of the post. A permanent magnet 40, which may be integrally molded into the post, or inserted in a recess formed in the post, is disposed along the longitudinal axis, the magnet having a length sufficient to extend at least over that portion of the length of the post encompassing slits 26a', 26b' and 26c' formed in the wall of the post. The magnet 32, in the form of a rod, has a diameter about one-fourth that of the post, and is of the type that is magnetized with positive and negative poles around its circumference and provides magnetic action along its entire length. The magnet is oriented in the post so that the magnetized portion confronts the inner ends of slits 26a', 26b' and 26c'.

A third construction of the post, which is functionally equivalent to the constructions shown in FIGS. 3 and 4, is illustrated in FIG. 5. In this embodiment, the post is molded, as by injection molding from a suitable plastic material, such as vinyl, having magnetic material incorporated therein. The magnetic material may be finely powdered Alnico metal, or Cermet, a magnetizable material which may be mixed with the plastic material and magnetized after the post is formed. As in the case of the other described constructions, the post has slits 26a'', 26b'' and 26c'' formed in the wall thereof, preferably inclined slightly to enhance the mechanical support for the bow portion of the clamp inserted therein.

A protective cover formed of clear plastic, for example, secured to the base with suitable securing means, may be provided, if desired, to enclose the posts and clamps, so that the whole unit can be transported from one place to another without risk of losing clamps in the process.

Another embodiment of the clamp organizer according to the invention is illustrated in FIG. 6 and includes a flat base member 29 formed, for example, of plastic material, on which is supported an upstanding columnar support member 31, which may also be formed of plastic. The base and support members may be of circular cross-section as shown, or of square or rectangular cross-section, if desired. The support member has a plurality of holes formed in the outer wall thereof, arranged in vertical columns, for example, four, as shown, uniformly distributed about the circumference of the support member, for receiving with a press fit a cylindrical post, nine of which are shown at 33, 35, 37, 39, 41, 43, 45, 47 and 49. The posts may have either of the alternative constructions illustrated in FIGS. 3, 4 or 5, and are preferably inclined slightly upwardly from the horizontal with the slits therein directed upwardly to enhance their mechanical holding of the bow portion of the dental clamp.

In use, the bow portion of a clamp is placed in a slit with its jaws extending outwardly from the post so as to be readily visible. The slit mechanically supports the bow over substantially its entire width, and the magnet by magnetic attraction retains the clamp in the slit, even though the organizer is subjected to jostling that would tend to dislodge the clamp from the slit if not otherwise held.

While there has been shown and described preferred and alternative embodiments of a dental clamp organizer in accordance with the invention, it will be appreciated that many changes and modifications may be made therein without, however, departing from the essential spirit thereof. For example, instead of the base member in FIG. 2 being rectangular in shape, it may be of other shapes, such as circular or oval, a different number of posts than has been shown may be used, or the posts may be of different lengths than have been suggested and formed of other materials.

I claim:

1. For use in supporting and systematically organizing according to shape and size a plurality of metal dental clamps of the type having a bow and a pair of legs a portable rack comprising:
    a support member, and
    at least one elongated post projecting from said support member,
    each said at least one post having at least one slit formed in its outer wall extending inwardly and substantially perpendicular to its longitudinal axis dimensioned to receive therein and support the bow portion of a dental clamp, and having contained therein permanent magnet material exposed at least at the inner end of said slit for retaining the dental clamp in the slit by magnetic attraction.

2. A portable rack according to claim 1, wherein said support member is a flat base member, and wherein said posts project perpendicularly from said base member and are arranged on said base member in rows and columns, and wherein the posts in successive rows are of increasing length and have an increasing number of substantially parallel spaced apart slits formed in the outer walls thereof.

3. A portable rack according to claim 1, wherein said support member is a vertically oriented columnar member, and wherein said posts project outwardly from said columnar member and are arranged in columns distributed about the outer surface of said columnar member.

4. A portable rack according to claim 2, wherein said slits, when said base member is horizontally oriented, extend radially inwardly and downwardly toward the longitudinal axis of the post.

5. A portable rack according to claim 1 or claim 2 or claim 3, wherein each of said posts is cylindrical in shape and has an internal cavity formed therein communicating with the inner end of a respective one of the slits formed therein, and a permanent magnet contained in each of said cavities and exposed at the inner end of its respective slit.

6. A portable rack according to claim 2 or claim 3, wherein said support member and said posts are formed of plastic material, wherein each of said posts has an internal cavity therein communicating with the inner end of a respective one of the slits formed therein, and a permanent magnet contained in each of said cavities and exposed at the inner end of its respective slit.

7. A portable rack according to claim 1 or claim 2 or claim 3, wherein said posts are formed of plastic material, and wherein each of said posts is cylindrical in shape and has an elongated permanent magnet contained therein disposed substantially on its longitudinal axis and of a length to be exposed at the inner ends of all of the slits formed in the post.

8. A portable rack according to claim 1 or claim 2 or claim 3, wherein said posts are formed of plastic material having particles of magnetic material incorporated therein.

* * * * *